（12) United States Patent
Ridley et al.

(10) Patent No.: US 8,252,300 B2
(45) Date of Patent: Aug. 28, 2012

(54) COPOLYMERS AND THEIR USE IN PERSONAL CARE COMPOSITIONS

(75) Inventors: Eleanor Bernice Ridley, Leeds (GB); Michael Green, Huddersfield (GB)

(73) Assignee: BASF SE, Ludwigshafen (DE)

( * ) Notice: Subject to any disclaimer, the term of this patent is extended or adjusted under 35 U.S.C. 154(b) by 116 days.

(21) Appl. No.: 10/523,242

(22) PCT Filed: Jul. 15, 2003

(86) PCT No.: PCT/EP03/07637
§ 371 (c)(1),
(2), (4) Date: Jan. 19, 2005

(87) PCT Pub. No.: WO2004/009662
PCT Pub. Date: Jan. 29, 2004

(65) Prior Publication Data
US 2005/0265948 A1    Dec. 1, 2005

(30) Foreign Application Priority Data
Jul. 22, 2002  (EP) ..................................... 02405633
Sep. 18, 2002  (EP) ..................................... 02020835

(51) Int. Cl.
*A61F 13/00*  (2006.01)
(52) U.S. Cl. ..................... 424/422; 424/70.1; 424/70.11
(58) Field of Classification Search ................. 424/422, 424/70, 47, 401, 49, 70.16; 526/303.1
See application file for complete search history.

(56) References Cited

U.S. PATENT DOCUMENTS

| | | | | |
|---|---|---|---|---|
| 4,419,344 A | | 12/1983 | Strasilla et al. ................. 424/70 |
| 4,440,744 A | | 4/1984 | Strasilla et al. ................. 424/70 |
| 4,454,114 A | | 6/1984 | Strasilla et al. ................. 424/70 |
| 4,460,567 A | | 7/1984 | Strasilla et al. ................. 424/70 |
| 4,460,568 A | | 7/1984 | Strasilla et al. ................. 424/70 |
| 4,460,569 A | | 7/1984 | Strasilla et al. ................. 424/70 |
| 4,460,570 A | | 7/1984 | Strasilla et al. ................. 424/70 |
| 5,665,368 A | * | 9/1997 | Lentini et al. ................. 424/401 |
| 6,365,656 B1 | * | 4/2002 | Green et al. ................. 524/313 |

FOREIGN PATENT DOCUMENTS

EP    247774 A2 * 12/1987
WO   WO 02/40622   *  5/2002

OTHER PUBLICATIONS

Principles of Polymerization, 3rd ed., John Wiley and Sons, Inc., Odian pp. 352-353.*
George Odian, "Principles of polymerization", 4$^{th}$ ed., pp. 367, John Wiley and Sons, Inc. , 2004.*
Odian, Principles of Polymerization, 3rd ed., 1991, John Wiley and Sons, Inc., pp. 350-371.*

* cited by examiner

Primary Examiner — James Rogers
(74) Attorney, Agent, or Firm — Shiela A. Loggins

(57) ABSTRACT

The present invention relates to a copolymer derived from the polymerization of a) at least one cationic monomer of formula (I), where in $R_1$ is hydrogen or methyl, $R_2$ is hydrogen or $C_1$-$C_4$alkyl, $R_3$, $R_4$ and $R_5$ are independently from each other hydrogen or $C_1$-$C_4$alkyl, n is a integer from 1-5, and Y is a counterion, and b) at least one monomer of formula (II) wherein $R_6$ signifies hydrogen or methyl, and $R_7$, $R_8$ and $R_9$ signify independently from each other hydrogen or $C_1$-$C_4$alkyl, with the proviso that at least one of the substituents $R_6$, $R_7$, $R_8$ and $R_9$ and $C_{1-4}$alkyl and c) optionally at least one cross-linking agent, which contains at least two ethylenically unsaturated moieties, as well as to their use in personal care product and to the personal care products.

$$R_1-CH=C(R_2)-C(=O)-O-(CH_2)_n-N^+(R_3)(R_4)(R_5) \quad Y \quad (I)$$

$$R_6-CH=C(R_7)-C(=O)-N(R_8)(R_9) \quad (II)$$

8 Claims, No Drawings

COPOLYMERS AND THEIR USE IN PERSONAL CARE COMPOSITIONS

This is a U.S. National Phase of International Application No. PCT/EP2003/07637, filed Jul. 15, 2003, published under WO2005/265948 on Dec. 1, 2005 which International Application takes priority from applications 02405633.5, filed Jul. 22, 2002 and 02020835.1, filed Sep. 18, 2002 both filed in the European Patent Office.

This invention relates to copolymers, their production and their use as rheology modifiers and as conditioner for water- and/or oil-based compositions, especially for water- and/or oil-based personal care products.

Rheology modifiers are used generally to adjust or modify the rheological properties of personal care compositions. Such properties include, without limitation, viscosity, flow rate, stability to viscosity change over time, and the ability to suspend particles in such personal care compositions.

Thickeners are used extensively in personal care compositions such as cosmetic and pharmaceutical formulations, to affect the aesthetics, product application and suspension and delivery of the active raw materials.

It is standard practice to include viscosifying (co-) polymers in personal care product composition in order to achieve optimum rheology characteristics. Various polymer types have been proposed for the purpose of increasing the viscosity of personal care compositions.

In U.S. Pat. No. 4,806,345 a copolymer consisting of a quaternary ammonium salt of a cross-linked dimethylamino-ethylmethacrylate and acrylamide for the use in personal care compositions is disclosed.

Although some copolymers used in personal care compositions described in the prior art do achieve viscosification of the composition, there is still a need to provide further improvement in rheology profile.

In addition to the rheology modifier properties mentioned in the prior art, the cationic nature of these copolymers impart substantivity to the negatively charged sites induced on the hair cuticle and stratum corneum by frictional forces, effects of UV radiation and use of chemical substances such as cleansing agents on the skin and hair. The conditioning properties of such copolymers is well known, and an increase in conditioning properties can be assessed by evaluation of the sensorial aspects of, for example, the hair, and in particular the effect on the wet and dry combing and wet and dry feel of the hair.

The aim of the present invention was to find a copolymer, which has advantages over the prior art in above-mentioned characteristics and other sensorial characteristics.

An embodiment of the present invention is a copolymer derived from the polymerization of (a) at least one cationic monomer of formula (I),

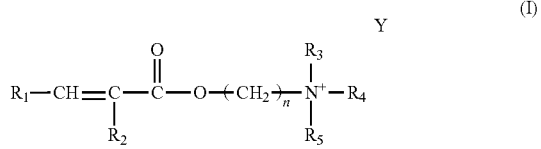

wherein
$R_1$ is hydrogen or methyl,
$R_2$ is hydrogen or $C_1$-$C_4$alkyl,
$R_3$, $R_4$ and $R_5$ are independently from each other hydrogen or $C_1$-$C_4$alkyl,
n is a integer from 1-5, and
Y is a counterion,
and
(b) at least one monomer of formula (II)

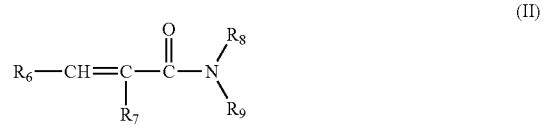

wherein
$R_6$ signifies hydrogen or methyl, and
$R_7$, $R_8$ and $R_9$ signify independently from each other hydrogen or $C_1$-$C_4$alkyl,
with the proviso that at least one of the substituents $R_6$, $R_7$, $R_8$ and $R_9$ is $C_{1-4}$alkyl and
(c) optionally at least one cross-linking agent, which contains at least two ethylenically unsaturated moieties.

Preferably, the copolymer consists of 20-95 weight-percent (wt-%) of at least one monomer of formula (I), more preferably of 40-90 wt-%, and of 5-50 wt-%, more preferably of 10-40 wt-% of at least one monomer of formula (II). The wt-% are based on the total weight of the polymer. The sum of the wt-% of the two components is always 100.

Preferably the copolymer comprises 50-500 ppm, more preferably 100-300 ppm, of at least one cross-linking agent based on the total amount of the copolymer.

Preferably, the monomer of formula (I) is characterized in that
$R_1$ is hydrogen or methyl, more preferably hydrogen,
$R_2$ is hydrogen or methyl, more preferably hydrogen,
$R_3$, $R_4$ and $R_5$ are independently from each other hydrogen or methyl, more preferably methyl,
n is an integer from 1-4, and
Y is Cl; Br; I; hydrogensulfate or methosulfate.

Preferably, the monomer of formula (II) is characterized in that
$R_6$ signifies hydrogen or methyl, more preferably hydrogen,
$R_7$ signifies hydrogen or methyl, more preferably hydrogen,
$R_8$ signifies hydrogen or methyl, more preferably methyl, and
$R_9$ signifies hydrogen or methyl, more preferably methyl,
with the proviso that at least one of the substituents $R_6$, $R_7$, $R_8$ and $R_9$ is methyl.

More preferably, the monomer of formula (I) is characterized in that
$R_1$ and $R_2$ signify hydrogen,
$R_3$, $R_4$ and $R_5$ signify methyl,
n is 1, 2 or 3, especially preferred 2 and
Y is Cl; Br; I; hydrogensulfate or methosulfate, especially preferred $Cl^-$.

More preferably, the monomer of formula (II) is characterized in that
$R_6$ and $R_7$ signify hydrogen,
$R_8$ and $R_9$ signify methyl.

A preferred embodiment of the present invention is a copolymer derived from the polymerization of (a) at least one cationic monomer of formula (I),

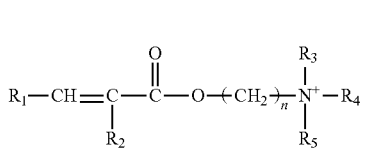

wherein
R₁, R₂, R₃, R₄ and R₅ are independently from each other hydrogen or methyl, n is 1, 2 or 3, and
Y is a counterion, preferably Cl; Br; I; hydrogensulfate or methosulfate,
and
(b) at least one monomer of formula (II)

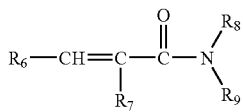

wherein
$R_6$ signifies hydrogen or methyl, more preferably hydrogen,
$R_7$ signifies hydrogen or methyl, more preferably hydrogen, and
$R_8$ and $R_9$ signify independently from each other hydrogen or methyl, more preferably methyl,
with the proviso that at least one of the substituents $R_6$, $R_7$, $R_8$ and $R_9$ is methyl,
and
(c) optionally at least one cross-linking agent selected from the group of tetra allyl ammonium chloride; allyl-acrylamides and allyl-methacrylamides; bisacrylamidoacetic acid and/or N,N'-methylene-bisacrylamide, preferably tetra allyl ammonium chloride and/or N,N'-methylene-bisacrylamide.

A more preferred embodiment of the present invention is a copolymer derived from the polymerization of
(a) 20-95 wt-% of at least one cationic monomer of formula (I), more preferably of 40-90 wt-% of at least one cationic monomer of formula (I),

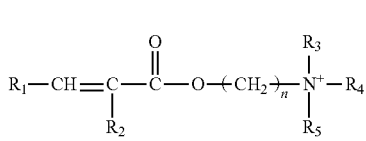

wherein
R₁ and R₂, are hydrogen,
R₃, R₄ and R₅ are independently from each other hydrogen or methyl,
n is 1, 2 or 3, and
Y is a counterion, preferably Cl; Br; I; hydrogensulfate or methosulfate,
and
(b) of 5-50 wt-%, more preferably of 10-40 wt-% of at least one monomer of formula (II)

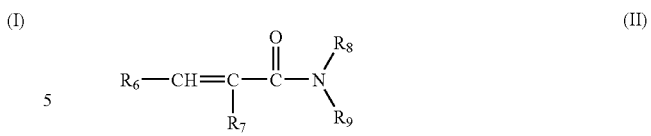

wherein
$R_6$ signifies hydrogen or methyl, more preferably hydrogen,
$R_7$ signifies hydrogen or methyl, more preferably hydrogen, and
$R_8$ signifies hydrogen or methyl, more preferably methyl, and
$R_9$ signifies hydrogen or methyl, more preferably methyl,
with the proviso that at least one of the substituents $R_6$, $R_7$, $R_8$ and $R_9$ is methyl,
and
(c) of 50-500 ppm (based on the total amount of monomers), more preferably of 100-300 ppm (based on the total amount of monomers) of at least one compound of the group of tetra allyl ammonium chloride; allyl-acrylamides and allyl-methacrylamides; bisacrylamidoacetic acid and/or N,N'-methylene-bisacrylamide, more preferably tetra allyl ammonium chloride and/or N,N'-methylene-bisacrylamide.

An especially preferred embodiment of the present invention is a copolymer derived from the polymerization of
(a) 20-95 wt-% of a cationic monomer of formula (I), more preferably of 40-90 wt-% of a cationic monomer of formula (I),

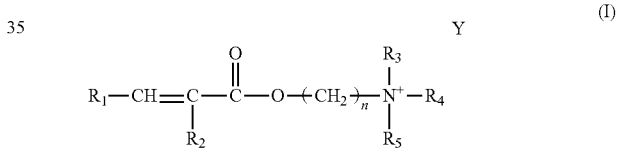

wherein
$R_1$, $R_2$, are hydrogen,
$R_3$, $R_4$ and $R_5$ are methyl,
n is 1, 2 or 3, preferably 2, and
Y is a counterion, preferably Cl; Br; I; hydrogensulfate or methosulfate, preferably Cl,
and
(b) of 5-50 wt-%, more preferably of 10-40 wt-% of a monomer of formula (II)

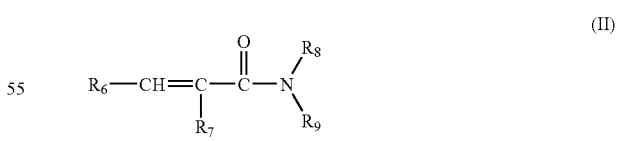

wherein
$R_6$ and $R_7$ signify hydrogen,
$R_8$ and $R_9$ signify methyl,
and
(c) of 100-300 ppm (based on the total amount of monomers) of tetra allyl ammonium chloride and/or N,N'-methylene-bisacrylamide.

A further embodiment is the use of a copolymer or a mixture thereof derived from the polymerization of (a) at least one cationic monomer of formula (I),

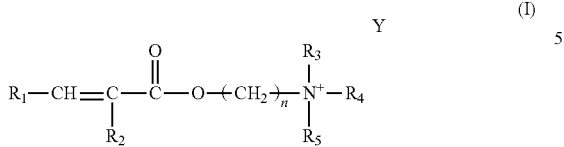

wherein
$R_1$ is hydrogen or methyl,
$R_2$ is hydrogen or $C_1$-$C_4$alkyl,
$R_3$, $R_4$ and $R_5$ are independently from each other hydrogen or $C_1$-$C_4$alkyl,
n is an integer from 1-5, and
Y is a counterion
and
(b) at least one monomer of formula (II)

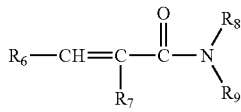

wherein
$R_6$ signifies hydrogen or methyl, and
$R_7$, $R_8$ and $R_9$ signify independently from each other hydrogen or $C_1$-$C_4$alkyl,
with the proviso that at least one of the substituents $R_6$, $R_7$, $R_8$ and $R_9$ is $C_1$-$C_4$alkyl,
and
(c) optionally at least one cross-linking agent, which contains at least two ethylenically unsaturated moieties
for water- and/or oil-based compositions, preferably for water- and/or oil-based personal care products.

A further preferred embodiment of the present invention is the use of copolymers consisting of 20-95 wt-% of at least one monomer of formula (I), more preferably of 40-90 wt-%, and of 5-50 wt-%, more preferably of 10-40 wt-% of at least one monomer of formula (II) for water- and/or oil-based compositions, preferably for water- and/or oil-based personal care products.

The wt-% are based on the total weight of the polymer.
The sum of the wt-% of the two components is always 100.
Preferably the copolymer comprises 50-500 ppm, more preferably 100-300 ppm, of at least one cross-linking agent based on the total amount of the copolymer.

A more preferred embodiment of the present invention is the use of above-mentioned copolymer wherein the monomer of formula (I) is characterized in that
$R_1$ is hydrogen or methyl, more preferably hydrogen,
$R_2$ is hydrogen or methyl, more preferably hydrogen,
$R_3$, $R_4$ and $R_5$ are independently from each other hydrogen or methyl, more preferably methyl,
n is an integer from 1-4, and
Y is Cl; Br; I; hydrogensulfate or methosulfate,
for water- and/or oil-based compositions, preferably for water- and/or oil-based personal care compositions.

A further more preferred embodiment of the present invention is the use of above-mentioned copolymer wherein monomer of formula (II) is characterized in that
$R_6$ signifies hydrogen or methyl, more preferably hydrogen,
$R_7$ signifies hydrogen or methyl, more preferably hydrogen, and
$R_8$ signifies hydrogen methyl, and
$R_9$ signifies hydrogen or methyl, more preferably methyl,
with the proviso that at least one of the substituents $R_6$, $R_7$, $R_8$ and $R_9$ is methyl, for water- and/or oil-based compositions, preferably for water- and/or oil-based personal care compositions.

An especially preferred embodiment of the present invention is the use of above-mentioned copolymer wherein the monomer of formula (I) is characterized in that
$R_1$ and $R_2$ are hydrogen,
$R_3$, $R_4$ and $R_5$ are methyl,
n is 1, 2 or 3, preferably 2 and
Y is Cl; Br; I; hydrogensulfate or methosulfate, preferably 2,
for water- and/or oil-based compositions, preferably for water- and/or oil-based personal care compositions.

A further especially preferred embodiment of the present invention is the use of above-mentioned copolymer wherein monomer of formula (II) is characterized in that
$R_6$ and $R_7$ signify hydrogen,
$R_8$ and $R_9$ signify hydrogen methyl,
for water- and/or oil-based compositions, preferably for water- and/or oil-based personal care compositions.

An important use is characterized in that a copolymer derived from the polymerization of
(a) a cationic monomer of formula (I),

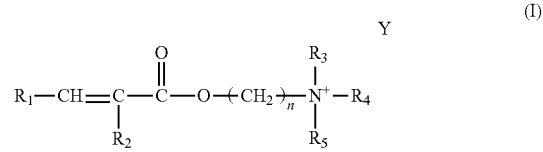

wherein
$R_1$, $R_2$, $R_3$, $R_4$ and $R_5$ are independently from each other hydrogen or methyl, n is 1, 2 or 3, and
Y is a counterion, preferably Cl; Br; I; hydrogensulfate or methosulfate,
and
(b) a monomer of formula (II)

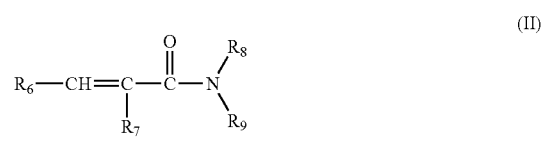

wherein
$R_6$ signifies hydrogen or methyl, more preferably hydrogen,
$R_7$ signifies hydrogen or methyl, more preferably hydrogen, and
$R_8$ signifies hydrogen or methyl, and
$R_9$ signifies methyl or hydrogen, more preferably methyl,
with the proviso that at least one of the substituent $R_6$, $R_7$, $R_8$ and $R_9$ is $C_1$-$C_4$alkyl,
and
(c) optionally at least one cross-linking agent selected from the group of tetra allyl ammonium chloride; allyl-acrylamides and allyl-methacrylamides; bisacrylamidoacetic acid and/or N,N'-methylene-bisacrylamide, preferably tetra allyl ammonium chloride and/or N,N'-methylene-bisacrylamide is used for water- and/or oil-based compositions, preferably for water- and/or oil-based personal care compositions.

A very important use is characterized in that a copolymer derived from the polymerization of (a) 20-95 wt-% of a cationic monomer of formula (I), more preferably of 40-90 wt-% of a cationic monomer of formula (I),

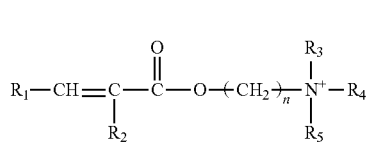

wherein $R_1$, $R_2$, $R_3$, $R_4$ and $R_5$ are independently from each other hydrogen or methyl, n is 1, 2 or 3, and Y is a counterion, preferably Cl; Br; I; hydrogensulfate or methosulfate, and (b) of 5-50 wt-%, more preferably of 10-40 wt-% of a monomer of formula (II)

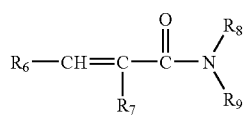

wherein $R_6$ signifies hydrogen or methyl, more preferably hydrogen, $R_7$ signifies hydrogen or methyl, more preferably hydrogen, and $R_8$ signifies hydrogen or methyl, and $R_9$ signifies hydrogen or methyl, more preferably methyl with the proviso that at least one of the substituent $R_6$, $R_7$, $R_8$ and $R_9$ is methyl, and (c) of 50-500 ppm (based on the total amount of monomers), more preferably of 100-300 ppm (based on the total amount of monomers) of at least one compound of the group of tetra allyl ammonium chloride; allyl-acrylamides and allyl-methacrylamides; bisacrylamidoacetic acid and/or N,N'-methylene-bisacrylamide, more preferably tetra allyl ammonium chloride and/or N,N'-methylene-bisacrylamide.

An especially important use is characterized in that a copolymer derived from the polymerization of (a) 20-95 wt-% of a cationic monomer of formula (I), more preferably of 40-90 wt-% of a cationic monomer of formula (I),

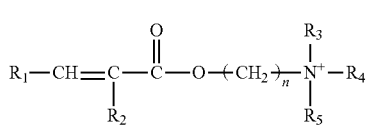

wherein $R_1$ and $R_2$ signify hydrogen $R_3$, $R_4$ and $R_5$ are methyl, n is 1, 2 or 3, preferably 2, and Y Cl; Br; I; hydrogensulfate or methosulfate, preferably Cl, and (b) of 5-50 wt-%, more preferably of 10-40 wt-% of a monomer of formula (II)

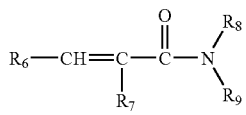

wherein $R_6$ and $R_7$ signify hydrogen and $R_8$ and $R_9$ signify methyl and (c) of 100-300 ppm (based on the total amount of monomers) of tetra allyl ammonium chloride and/or N,N'-methylene-bisacrylamide.

The thickener-rheology modifier system of this invention is useful in personal care compositions and more particularly in hair care and skin care compositions. These compositions will generally comprise at least one cosmetically-functional agent used in an amount effective to impart desired cosmetic properties to the personal care composition. The term "cosmetically-functional agent", as used herein, means any material, compound or composition applied to the hair or skin for cosmetic application thereof. Exemplary agents include emollients, humectants, lubricants, UV-light inhibitors, preservatives, pigments, dyes, colorants, alpha-hydroxy acids, aesthetic enhancers such as starch, perfumes and fragrances, film formers (water proofing agent), antiseptics, antifungal, antimicrobial and other medicaments, solvents, surfactants, natural or synthetic polymers, hair conditioning agents and hair fixatives. Such cosmetically-functional agents include mineral oils, glycerin, beeswax, lanolin, acetylated lanolin, stearic acid, palmitic acid, cetyl alcohol, sodium salts of olefin sulfonates, various proteins, polymeric sugars, conditioning agents such as polyquaterniun and hair fixatives such as poly(vinyl pyrrolidone) and N-vinyl formamide or polyvinyl formamide.

The cosmetically-functional agent may be present in the personal care composition in an amount of up to 60 wt-% (the wt-% based on the total weight of the personal care composition.

Personal care compositions are for example shampoos, bath- and shower additives, hair-care products, wax/fat compositions, liquid soaps, lotions, gels, crèmes, deodorants, stick preparations, powders, ointments, other aqueous or alcoholic or aqueous/alcoholic solutions, for example cleaning solutions for the skin, moist cleaning sheets and oils.

Personal care compositions include a very wide range of products. Suitable products are, for example, especially the following:

skin-care products, for example skin washing and cleansing products in the form of bars of soap or liquid soaps, syndets or washing pastes, bath products, for example liquid (foam baths, milks, shower products) or solid bath products, such as bath pearls and bath salts;

skin-care products, such as skin emulsions, multiple emulsions or skin oils;

decorative body-care products, for example face make-ups in the form of day or powder creams, face powders (lose and compressed), rouge or cream make-ups, eye-care products, for example eye shadow products, mascara, eyeliners, eye creams or eye-fix creams; lip-care products, for example lipstick, lip gloss, lip liner, nail-care products, such as nail varnish, nail varnish remover, nail hardeners or cuticle removers;

feminine hygiene products, such as feminine hygiene washing lotions or sprays;

foot-care products, for example foot baths, foot powders, food creams or foot balms, special deodorants and antiperspirants or products for scrubbing off callouses;

sunscreens, such as sun milks, lotions, creams, oils, sunblockers or tropicals, pre-sun products or after-sun products;

suntanning products, for example self-tanning creams;

depigmenting products, for example products for bleaching or lightening skin;

insect repellents, for example insect oils, lotions, sprays or sticks;

deodorants, for example deodorant sprays, non-aerosol sprays, deodorant gels, sticks or roll-ons;

antiperspirants, for example antiperspirant sticks, creams or roll-ons;

products for cleansing and treating impure skin, for example syndets (solid or liquid), peeling or scrubbing products or peeling masks;

chemical depilatory products, for example depilatory powders, liquid depilatory products, creamy or pasty depilatory products, depilatory gels or aerosol foams;

shaving products, for example shaving soap, foaming shaving creams, non-foaming shaving creams, shaving foams and gels, preshaving products for dry shaving, aftershaves or aftershave lotions;

scents, for example perfumes (Eau de Cologne, Eau de Toilette, Eau de Parfum, Parfum de Toilette, perfume), perfume oils or perfume creams;

products for oral and dental hygiene as well as for dentures, for example toothpastes, tooth gels, tooth powders, mouth-wash concentrates, anti-plaque mouth-washes, denture cleaning products or denture adhesion products;

cosmetic formulations for hair treatment, for example hair washes in the form of shampoos, hair conditioners, hair-care products, for example pretreatment products, hair tonics, hair styling creams and gels, pomades, hair rinses, deep conditioning treatments, intensive hair care treatments, hair setting products, for example waving agents for perms (hot wave, mild wave, cold wave), hair straightening products, liquid hair fixatives, hair foams, hair sprays, bleaching agents, for example hydrogen peroxide solutions, bleaching shampoos, bleaching creams, bleaching powders, bleaching pastes or oils, temporary, semitemporary or permanent hair dyes, products containing self-oxidizing dyes, or natural hair dyes, such as henna or camomile.

The personal care compositions listed above can be in a very wide range of forms of presentation, for example in the form of liquid formulations as an oil/water (O/W) emulsion, in the form of a gel, in the form of an oil, cream, milk or lotion, in the form of a powder, lacquer, pellets or make-up, in the form of a stick, in the form of a spray (spray with propellant or pumping spray) or an aerosol, in the form of a foam, or in the form of a paste.

The oral hygiene composition may comprise an additional antibacterial enhancing agent, for example an anionic polymeric polycarboxylate, a dehydrated polyphosphate salt, a compound which provides a source of fluoride ions, a polishing material, including siliceous material or sodium bicarbonate, an orally acceptable vehicle, including a water-phase with humectants, thickeners, surface-active agents and a flavoring or sweetening material.

The oil phase (oil-component) can be chosen from the following substance groups without limiting the kind of lipophilic ingredient to those substances:

Fatty alcohols: Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of $C_{12}$-$C_{15}$ alcohols, acetylated lanolin alcohol, etc.

Esters of fatty acids: esters of linear $C_6$-$C_{24}$ fatty acids with linear $C_3$-$C_{24}$ alcohols, esters of branched $C_6$-$C_{13}$ carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxo-synthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butylstearate, n-hexyllaurate, n-decyloleate, isooctylstearate, iso-nonylstearate, isononyl isononanoate, 2-ethylhexylpalmitate, 2-hexyllaurate, 2-hexyldecylstearate, 2-octyidodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Further oil components that can be used are dicarboxylic acid esters, such as diethylhexyl 2,6-naphthalate, di-n-butyl adipate, di(2-ethylhexyl)-adipate, di(2-ethylhexyl)-succinate and diisotridecyl acelate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated and/or unsaturated, especially benzoic acid, esters of $C_2$-$C_{12}$dicarboxylic acids with linear or branched alcohols having from 1 to 22 carbon atoms or polyols having from 2 to 10 carbon atoms and from 2 to 6 hydroxy groups.

Natural or synthetic triglycerides including glyceryl esters and derivatives. Di- or triglycerides, based on $C_6$-$C_{18}$ fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil (Ricinus Communis), hydrogenated vegetable oil, sweet almond oil, wheat germ oil, sesame oil, hydrogenated cottonseed oil, coconut oil, avocado oil, corn oil, hydrogenated castor oil, shea, butter, cocoa butter, soybean oil, mink oil, sunflower oil, safflower oil, macadamia nut oil, olive oil, hydrogenated tallow, apricot kernel oil, hazelnut oil, borago oil, etc.

Waxes including esters of long-chain acids and alcohols as well as compounds having wax-like properties, e.g., carnauba wax (Copernicia Cerifera), beeswax (white or yellow), lanolin wax, candellila wax (Euphorbia Cerifera), ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent waxes: Ikylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon oils: mineral oil (light or heavy), petrolatum (yellow or white), microcrystalline wax, paraffinic and isoparaffinic compounds, hydrogenated isoparaffinic molecules as polydecenes, and polybutene, hydrogenated polyisobutene, squalane, isohexadecane, isododecane and others from plant and animal kingdom.

Silicones or siloxanes (organosubstituted polysiloxanes): dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes: dimethicone such as Dow Corning® 200 fluid, Mirasil® DM (Rhodia), dimethiconol. Cyclic silicone fluids: cyclopentasiloxanes volatiles such as Dow Corning® 345 fluid, Silbione® grade, Abil® grade. Phenyltrimethicone; Dow Corning® 556 fluid. Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Very suitable as well are nonvolatile organopolysiloxanes as disclosed by U.S. Pat. No. 5,637,306 (column 2, line 12-column 4, line 5). Such nonvolatile organopolysiloxane are selected from the group consisting of polyalkylsiloxanes, polyarylsiloxanes, polyalkylarylsiloxanes, modified and unmodified polysiloxanes, silicone gums and resins, and organomodified polysiloxanes, with the exception of polysiloxanes carrying polyethyleneoxy and/or polypropyleneoxy or carboxylate or bisulfite groups organopolysiloxane Preferably these nonvolatile organopolysiloxanes are selected from the group consisting of:

A) polyalkyl ($C_1$-$C_{20}$) siloxanes; linear polydimethylsiloxanes containing end trimethylsilyl groups and linear polydimethylsiloxanes containing end trihydroxysilyl groups;

B) linear and/or branched polydimethylphenylsiloxanes or polydimethyldiphenylsiloxanes, with a viscosity of $10^{-5}$ to $5.10^{-2}$ M$^2$/s at 25° C.;

C) gums used alone or in the form of a mixture in a solvent, selected from the group consisting of the following compounds:

polydimethylsiloxane, optionally hydroxylated at the chain end,
poly [(dimethylsiloxane)/(methylvinylsiloxane)],
poly [(dimethylsiloxane)/(diphenylsiloxane)],
poly [(dimethylsiloxane)/(phenylmethylsiloxane)],
poly [(dimethylsiloxane)/(diphenylsiloxane)/(methylvinylsiloxane)];

and the following mixtures;

the mixtures formed from a polydimethylsiloxane hydroxylated at the chain end and from a cyclic polydimethylsiloxane;

the mixtures formed from a polydimethylsiloxane gum and from a cyclic silicone;

the mixtures of two polydimethylsiloxanes of different viscosities; and

D) the organopolysiloxane resins containing the (R)$_2$SiO$_{2/2}$, RSiO$_{3/2}$ and SiO$_{4/2}$ units, in which R represents a hydrocarbon group having 1 to 6 carbon atoms or a phenyl group.

Fluorinated or perfluorinated oils: perfluorhexane, dimethylcyclohexane, ethylcyclopentane (Flutec® grades). polyperfluoromethylisopropyl ether (Fomblin® grades) The oil components can be used in an amount of up to 99 wt-%.

In an O/W-formulation the oil component is preferably present in an amount of from 5 wt-% to 50 wt-% and more preferably from 10 wt-% to 35 wt-%, based on the total weight of the personal care composition.

Emulsifiers. Any conventionally usable emulsifier can be used for the personal care compositions. Emulsifier systems may comprise for example:

Carboxylic acids and their salts: alcalin soap of sodium, potassium and ammonium, metallic soap of calcium or magnesium, organic basis soap such as Lauric, palmitic, stearic and oleic acid etc. . . .

Alkyl phosphates or phosphoric acid esters: acid phosphate, diethanolamine phosphate, potassium cetyl phosphate.

Ethoxylated Carboxylic Acids or Polyethyleneglycol esters (PEG-n Acylates). Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group. Fatty alcohol Polyglycolether such as Laureth-n, Ceteareth-n, Steareth-n, Oleth-n. Fatty acid polyglycolether such as PEG-n Stearate, PEG-n Oleate, PEG-n Cocoate Monoglycerides and Polyol esters. $C_{12}$-$C_{22}$ fatty acid mono- and di-esters of addition products of from 1 to 30 mol of ethylene oxide with polyols Fatty acid and polyglycerol ester such as Monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as Monostearate diethylene glycol, Fatty acid and Polyethylene glycol esters, Fatty acid and saccharose esters such as Sucro esters, glycerol and saccharose esters such as Sucro glycerides Sorbitol and sorbitan: Sorbitan mono- and di-esters of saturated and unsaturated fatty acids having from 6 to 22 carbon atoms and ethylene oxide addition products Polysorbate-n series, Sorbitan esters such as Sesquiisostearate, sorbitan, PEG-(6)-isostearate sorbitan, PEG-(10)-Sorbitan laurate, PEG-17-dioleate sorbitan.

Glucose derivatives: $C_8$-$C_{22}$ alkyl-mono and oligo-glycosides and ethoxylated analogues with glucose being preferred as the sugar component. O/W emulsifiers such as Methyl Gluceth-20sesquistearate, Sorbitan Stearate/Sucrose Cocoate, Methyl Glucose Sesquistearate, Cetearyl alcohol/Cetearyl glucoside. W/O emulsifiers such as Methyl glucose Dioleate/Methyl glucose isostearate.

Sulfates and sulfonated derivatives: Dialkylsulfosuccinates (DOSS: Dioctyl succinate), alkyl lauryl sulfonate, linear sulfonated parafins, sulfonated tetrapropylene sulfonate, sodium lauryl sulfates, ammonium and ethanolamine lauryl sulfates, lauryl ether sulfates, sodium laureth sulfates, sulfosuccinates, acetyl isothionates, alkanolamide sulfates such as Taurines, Methyl taurines, Imidazole sulfates.

Amine derivatives: amine salts, ethoxylated amines such as Oxide amine, with chains containing an heterocycle such as alkyl imidazolines, pyridine derivatives, isoquinoteines, cetyl pyridinium chlorure, cetyl pyridinium bromure, quaternary ammonium such as cetyltrimethylbromure ammonium bromure (CTBA), Stearylalkonium.

Amide derivatives.alkanolamides such as acylamide DEA, ethoxylated amides, such as PEG-n acylamide, oxydeamide.

Polysiloxane/Polyalkyl/Polyether Copolymers and derivatives: dimethicone, copolyols, silicone polyethylene Oxide copolymer, silicone glycol copolymer.

Propoxylated or POE-n ethers (Meroxapols), Polaxamers or poly(oxyethylene)m-block-poly(oxypropylene)n-block (oxyethylene)

Zwitterionic surfactants that carry at least one quaternary ammonium group and at least one carboxylate and/or sulfonate group in the molecule. Zwitterionic surfactants that are especially suitable are the so-called betaines, such as N-alkyl-N,N-dimethylammonium glycinates, for example cocoalkyidimethylammonium glycinate, N-acylaminopropyl-N,N-dimethylammonium glycinates, for example cocoacylaminopropyidimethylammonium glycinate, and 2-alkyl-3-carboxymethyl-3-hydroxyethylimidazolines each having from 8 to 18 carbon atoms in the alkyl or acyl group and also cocoacylaminoethylhydroxyethyl-carboxy-methylglycinate, N-alkylbetaine, N-alkylaminobetaines.

Alkylimidazolines, alkylopeptides, lipoaminoacides

Self emulsifying bases (.K:F:DePolo—A short textbook of cosmetology, Chapter 8, Table 8-7, p 250-251):

Non ionic bases such as PEG-6 Beeswax (and) PEG-6 Stearate (and) polyglyceryl-2 isostearate [Apifac], Glyceryl stearate (and) PEG-100 stearate. [Arlacel 165], PEG-5 Glyceryl stearate [arlatone 983 S], Sorbitan oleate (and) Polyglyceryl-3 Ricinoleate.[Arlacel 1689], Sorbitan Stearate and sucrose cocoate [arlatone 2121], Glyceryl stearate and laureth-23 [Cerasynth 945], Cetearyl alcohol and ceteth-20 [Cetomacrogol Wax], Cetearyl alcohol and Polysorbate 60 and PEG-150 and stearate-20[Polawax GP 200, Polawax NF], Cetearyl alcohol and cetearyl polyglucoside [Emulgade PL 1618], Cetearyl alcohol and ceteareth-20 [Emulgade 1000NI, Cosmowax], Cetearyl alcohol and PEG-40 castor oil [Emulgade F Special], Cetearyl Alcohol and PEG-40 Castor Oil and Sodium Cetearyl Sulfate [Emulgade F], Stearyl Alcohol and Steareth-7 and Steareth-10 [Emulgator E 2155], Cetearyl Alcohol and Szeareth-7 and steareth-10 [Emulsifying wax U.S.N.F], Glyceryl stearate and PEG-75 stearate [Gelot 64], Propylene Glycol ceteth-3 Acetate .[Hetester PCS], Propylene Glycol isoceth-3 Acetate [Hetester PHA], Cetearyl alcohol and Ceteth-12 and oleth-12 [Lanbritol Wax N 21], PEG-6 Stearate and PEG-32 Stearate [Tefose 1500], PEG-6 Stearate and ceteth-20 and steareth-20 [Tefose 2000], PEG-6 Stearate and ceteth-20 and Glyceryl Stearate and steareth-20 [Tefose 2561], Glyceryl Stearate and ceteareth-20 [Teginacid H, $C_1$ X].

Anionic alkaline bases such as PEG-2 Stearate SE, Glyceryl stearate SE [Monelgine, Cutina KD], Propylene glycol stearate [Tegin P].

Anionic acid bases such as Cetearyl Alcohol and Sodium cetearyl sulfate [Lanette N, Cutina LE, Crodacol GP], Cetearyl Alcohol and sodium Lauryl Sulfate [Lanette W], Trilaneth-4 Phosphate and glycol stearate and PEG-2 Stearate [Sedefos 75], Glyceryl stearate and sodium lauryl Sulfate [Teginacid Special].

Cationic acid bases such as cetearyl Alcohol and cetrimonium bromide.

The emulsifiers may be used in an amount of, for example, from 1 wt-% to 30 wt-%, especially from 4 wt-% to 20 wt-% and preferably from 5 wt-% to 10 wt-%, based on the total weight of the composition.

When formulated in O/W emulsions, the preferably amount of such emulsifier system could represent 5% to 20% of the oil phase.

Adjuvants and additives. The personal care compositions, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, consistency regulators, additional thickeners, polymers, stabilizers, biogenic active ingredients, deodorizing active ingredients, anti-dandruff agents, film formers, swelling agents, further UV light-protective factors, antioxidants, hydrotropic agents, preservatives, insect repellents, self-tanning agents, solubilizers, perfume oils, colourants, bacteria-inhibiting agents and the like.

The adjuvants and additives may optionally be present in the personal care composition in an amount of, for example, from 0.1 wt-% to 25 wt-% based on the total weight of the composition.

Super-fatting agents. Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilizers.

Surfactants. Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isothionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency regulators/Additional Thickeners and Rheology modifiers. As additional thickeners and rheology modifiers, there come into consideration the groups of silicium dioxide, magnesium silicates, aluminium isilicates, polysaccharides or derivatives thereof for example hyaluronic acid, xanthan gum, guar-guar, agar-agar, alginates, Carraghenan, gellan, pectines, or modified cellulose such as hydroxycellulose, hydroxypropylmethylcellulose. In addition polyacrylates or homopolymer of reticulated acrylic acids and polyacrylamides, e.g. the Carbopol range (e.g. Carbopol types 980, 981, 1382, ETD 2001, ETD2020, Ultrez 10; INCI: Carbomer) or Salcare range such as Salcare SC80 (Steareth-10 Allyl Ether/Acrylates Copolymer), Salcare SC81 (Acrylates copolymer), Salcare SC91 and Salcare AST (Sodium Acrylates Copolymer/PPG-1 trideceth-6), Sepigel 305 (Polyacrylamide/laureth-7), Simulgel NS and Simulgel EG (Hydroxyethyl Acrylate/Sodium Acryloyldimethyl Taurate Copolymer), Stabilen 30 (Acrylates/Vinyl Isodecanoate Crosspolymer), Pemulen TR-1(Acrylates/$C_{10}$-$C_{30}$ Alkyl Acrylate Crosspolymer), Luvigel EM (Sodium Acrylates Copolymer), Aculyn 28 (Acrylates/Beheneth-25 Methacrylate Copolymer), etc.

Polymers. Suitable cationic polymers are, for example, cationic cellulose derivatives, for example a quaternized hydroxymethyl cellulose obtainable under the name Polymer JR 400® from Amerchol, cationic starches, copolymers of diallylammonium salts and acrylamides, quaternized vinylpyrrolidone/vinyl imidazole polymers, for example Luviquat® (BASF), condensation products of polyglycols and amines, quaternized collagen polypeptides, for example lauryldimonium hydroxypropyl hydrolyzed collagen (Lamequat®L/Grünau), quaternised wheat polypeptides, polyethyleneimine, cationic silicone polymers, for example amidomethicones, copolymers of adipic acid and dimethylaminohydroxypropyidiethylenetriamine (Cartaretin®/ Clariant), copolymers of acrylic acid with dimethyldiallylammonium chloride (Merquat® 550/Chemviron), polyaminopolyamides, as described, for example, in FR-A-2 252 840, and the cross-linked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar® C-17, Jaguar® C-16 from Celanese, quaternised ammonium salt polymers, for example Mirapol® A-15, Mirapol® AD-1, Mirapol® AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/ butyl maleate/isobornyl acrylate copolymers, methyl vinyl ether/maleic anhydride copolymers and esters thereof, uncrosslinked polyacrylic acids and polyacrylic acids cross linked with polyols, acrylamidopropyltrimethylammonium chloride/acrylate copolymers, octyl acrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethyl-aminoethyl methacrylate/vinyl caprolactam terpolymers and also optionally derivatised cellulose ethers and silicones. Furthermore the polymers as described in EP 1093796 (pages 3-8, paragraphs 17-68) may be used.

Biogenic active ingredients. Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorizing active ingredients. As deodorizing active ingredients there come into consideration, for example, antiperspirants, for example aluminium chlorohydrates (see J. Soc. Cosm. Chem. 24, 281 (1973)). Under the trade mark Locron® of Clariant, there is available commercially, for example, an aluminium chlorohydrate corresponding to formula $Al_2(OH)_5Cl \times 2.5\ H_2O$, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorizing active ingredients. Such inhibitors are preferably trialkyl citrates, such as trimethyl citrate, tripropyl citrate, triisopropyl citrate, tributyl citrate and especially triethyl citrate (Hydagen® CAT, Henkel KGaA, Düsseldorf/GER), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlorhexidine gluconate. 5-Chloro-2-(2,4-dichlorophenoxy)-phenol (Irgasan®, Ciba Specialty Chemicals Inc.) has also proved especially effective.

Anti-dandruff agents. As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Antioxidants.

The personal care product can optionally contain one or more antioxidants. Any common antioxidant can be used.

Typical examples of such antioxidants are 4,4'-di-α-cumyl-diphenylamine, mono- and dialkylated tert-butyl/tert-octyl-diphenylamines, n-octadecyl 3,5-di-tert-butyl-4-hydroxyhydrocinnamate, Tetradibutyl pentaerythrityl-4-hydroxyhydrocinnamate, neopentanetetrayl tetrakis(3,5-di-tert-butyl-4-hydroxyhydrocinammate), di-n-octa-decyl 3,5-di-tert-butyl-4-hydroxybenzylphosphonate, 1,3,5-tris(3,5-di-tert-butyl-4-hydroxybenzyl)isocyanurate thiodiethylene bis(3,5-di-tert-butyl-4-hydroxyhydro-cinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3-tris(2-methyl-4-hydroxy-5-tert-butyl-phenyl)butane, 1,3,5-tris[2-(3,5-di-tert-butyl-4-hydroxyhydrocinnamoy)oxy)ethyl]iso-cyanurate, 3,5-di-(3,5-di-tert-butyl-4-hydroxybenzyl)mesitol, hexamethylene bis(3,5-di-tertbutyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)-hydrazide, N,N'-bis[2-(3,5-di-tert-butyl-4-hydroxyhydrocinnamoyloxy)-ethyl]oxamide, and N,N-dialkylhydroxylamine prepared from di(hydrogenated tallow)amine by direct oxidation.

Further suitable antioxidants areamino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes (e.g. β-carotene, β-carotene, lycopene) and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine), also (metal) chelating agents (e.g. α-hydroxy fatty acids, palmitic acid phytic acid, lactoferrin), α-hydroxy acids (e.g. citric acid, lactic acid, malic acid), humic acid, bile acid, bile extracts, biliverdin, EDTA, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, α-glycosylrutin, ferulic acid, furfurylidene glucitol, carnosine, butyl hydroxytoluene, butyl hydroxyanisole, nordihydroguaiaretic acid, trihydroxy-butyrophenone, uric acid and derivatives thereof, mannose and derivatives thereof, superoxide dismutase, N-[3-(3,5-di-tert-butyl-4-hydroxyphenyl)propionyl]-sulfanilic acid (and salts thereof, for example the disodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives (salts, esters, ethers, sugars, nucleotides, nucleosides, peptides and lipids) of HALS (="Hindered Amine Light Stabilizers") compounds may also be mentioned.

The amount of antioxidants present is usually from 0.001 wt-% to 25 wt-%, preferably from 0.01 wt-% to 3 wt-%, based on the weight of the personal care product.

Hydrotropic agents. To improve the flow behaviour it is also possible to employ hydrotropic agents, for example ethoxylated or non ethoxylated mono-alcohols, diols or polyols with a low number of C-atoms or their ethers (e.g. ethanol, isopropanol, 1,2-dipropanediol, propyleneglycol, glycerine, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 wt-% to 50 wt-%; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives and Bacteria-inhibiting agents. Suitable preservatives include, for example, methyl-, ethyl-, propyl-, butyl-parabens, Benzalkonium chloride, 2-Bromo-2-nitropropane-1,3-diol, Dehydroacetic acid, Diazolidinyl Urea, 2-Dichloro-benzyl alcohol, DMDM hydantoin, Formaldehyde solution, Methyldibromoglutanitrile, Phenoxyethanol, Sodium Hydroxymethylglycinate, Imidazolidinyl Urea and Triclosan and further substance classes listed in the following reference: K.:F.DePolo—A short textbook of cosmetology, Chapter 7, Table 7-2, 7-3, 7-4 and 7-5, p 210-219.

Bacteria-inhibiting agents. Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenylbiguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorizing agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 wt-% to 2 wt-%, based on the solids content of the preparations.

Perfume oils. There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, α,α-isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, α,α-hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, α-damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Colourants. There may be used as colourants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106. The colourants are usually used in concentrations of from 0.001 wt-% to 0.1 wt-%, based on the total mixture.

Other adjuvants. It is furthermore possible for the personal care composition to contain, as adjuvants, anti-foams, such as silicones, structurants, such as maleic acid, solubilisers, such as ethylene glycol, propylene glycol, glycerol or diethylene glycol, opacifiers, such as latex, styrene/PVP or styrene/acrylamide copolymers, complexing agents, such as EDTA, NTA, alaninediacetic acid or phosphonic acids, propellants, such as propane/butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or mercaptoethanesulfonic acid, or oxidizing agents, such as hydrogen peroxide, potassium bromate or sodium bromate.

There come into consideration as insect repellents, for example, N,N-diethyl-m-toluamide, 1,2-pentanediol or insect repellent 3535; suitable self-tanning agents are, for example, dihydroxyacetone and/or erythrulose or dihydroxy acetone and/or dihydroxy acetone precursors as described in WO 01/85124 and/or erythrulose.

Ultraviolet Light Absorbers

Ultraviolet Light Absorbers (UV absorbers) are employed in cosmetics to protect the product from chemical or physical deterioration induced by ultraviolet light. Sunscreen Agents are OTC drug ingredients, which protect the skin from ultraviolet light. UV absorbers, like sunscreen agents, have the ability to convert incident ultraviolet radiation into less damaging infrared radiation (heat). Suitable UV absorbers are, for example:

Acetaminosalol, Allantoin PABA, Benzalphthalide, Benzophenone, Benzophenone-1, Benzophenone-2, Benzophenone-3, Benzophenone-4, Benzophenone-5, Benzophenone-6, Benzophenone-7, Benzophenone-8, Benzophenone-9, Benzophenone-10, Benzophenone-11, Benzophenone-12, Benzotriazolyl Dodecyl p-Cresol, 3-Benzylidene Camphor, Benzylidenecamphor Hydrolyzed Collagen Sulfonamide, Benzylidene Camphor Sulfonic Acid, Benzyl Salicylate, Bis-Ethylhexyloxyphenol Methoxyphenyl Triazine, Bornelone, Bumetrizole, Butyl Methoxydibenzoylmethane, Butyl PABA, Callophyllum Inophyllum Seed Oil, Camellia Sinensis Leaf Extract, Carotenoids, Ceria/Silica, Ceria/Silica Talc, Cinoxate, DEA-Methoxycinnamate, Dibenzoxazoyl Naphthalene, Di-t-Butyl Hydroxybenzylidene Camphor, Diethylhexyl Butamido Triazone, Diethylhexyl 2,6-Naphthalate, Digalloyl Trioleate, Diisopropyl Methyl Cinnamate, 1-(3,4-Dimethoxyphenyl)-4,4-Dimethyl-1,3-Pentanediene, Dimethyl PABA Ethyl Cetearyldimonium Tosylate, Dimorpholinopyridazinone, Diphenyl Carbomethoxy Acetoxy Naphthopyran, Disodium Bisethylphenyl Triaminotriazine Stilbenedisulfonate, Disodium Distyrylbiphenyl Disulfonate, Disodium Phenyl Dibenzimidazole Tetrasulfonate, Drometrizole, Drometrizole Trisiloxane, Esculin, Ethyl Dihydroxypropyl PABA, Ethyl Diisopropylcinnamate, Ethylhexyl Dimethoxybenzylidene Dioxoimidazolidine Propionate, Ethylhexyl Dimethyl PABA, Ethylhexyl Ferulate, Ethylhexyl Methoxycinnamate, Ethylhexyl Salicylate, Ethylhexyl Triazone, Ethyl Methoxycinnamate, Ethyl PABA, Ethyl Urocanate, Etocrylene, Ferulic Acid, 4-(2-Beta-Glucopyranosiloxy) Propoxy-2-Hydroxybenzophenone, Glyceryl Ethylhexanoate Dimethoxycinnamate, Glyceryl PABA, Glycol Salicylate, Hexanediol salicylate, Homosalate, Hydrolyzed Lupine Protein, Isoamyl p-Methoxycinnamate, Isopentyl Trimethoxycinnamate Trisiloxane, Isopropylbenzyl Salicylate, Isopropyl Dibenzoylmethane, Isopropyl Methoxycinnamate, Menthyl Anthranilate, Menthyl Salicylate, 4-Methylbenzylidene Camphor, Methylene Bis-Benzotriazolyl Tetramethylbutylphenol, Octocrylene, Octrizole, PABA, PEG-25 PABA, Pentyl Dimethyl PABA, Phenylbenzimidazole Sulfonic Acid, Pinus Pinaster Bark Extract, Polyacrylamidomethyl Benzylidene Camphor, Polysilicone-15, Potassium Methoxycinnamate, Potassium Phenylbenzimidazole Sulfonate, Red Petrolatum, Sodium Benzotriazolyl Butylphenol Sulfonate, Sodium Isoferulate, Sodium Phenylbenzimidazole Sulfonate, Sodium Urocanate, Spirulina Platensis Powder, TEA-Phenylbenzimidazole Sulfonate, TEA-Salicylate, Terephthalylidene Dicamphor Sulfonic Acid, Tetrabutyl Phenyl Hydroxybenzoate, Titanium Dioxide, Tocotrienols, TriPABA Panthenol, Urocanic Acid, VA/Crotonates/Methacryloxybenzophenone-1 Copolymer and Vitis Vinifera (Grape) Seed Extract.

Polymeric beads or hollow spheres as SPF enhancers. The combination of the UV-absorbers described above, with SPF enhancers, such as non-active ingredients like Styrene/acrylates copolymer, silica beads, spheroidal magnesium silicate, spherical polyamide powder such as n-lactam polymer (Orgasol® range, Elf Atochem) cross linked Polymethylmethacrylates (PMMA; Micopearl M305 Seppic), can maximize better the UV protection of the sun products. Holosphere additives (Sunspheres® ISP, Silica Shells Kobo.) deflect radiation and the effective path length of the photon is therefore increased.(EP0893119). Some beads, as mentioned previously, provide a soft feel during spreading. Moreover, the optical activity of such beads, e.g.Micropearl M305, cans modulate skin shine by eliminating reflection phenomena and indirectly may scatter the UV light.

When formulated in O/W emulsions, the preferably amount of such SPF enhancers should represent 1 wt-% to 10 wt-% of the total amount of the personal care composition.

A typical O/W-based personal care composition comprises:
0.5-10 wt-% of at least one of the inventive copolymer
2-25 wt-% of at least one oil-component,
0-25 wt-% of at least one adjuvant and/or additive,
water up to 100 wt-%.

A typical oil-based personal care composition comprises
0.5-10 wt-% of at least one of the inventive copolymer
50-99 wt-% of at least one oil-component,
0-25 wt-% of at least one adjuvant and/or additive.

An soap has, for example, the following composition:
0.1 to 5% wt-% of at least one inventive copolymer
0.3 to 1% wt-% of titanium dioxide
1 to 10% wt-% of stearic acid
to 100 wt-% of soap base, for example the sodium salts of tallow fatty and coconut fatty acid or glycerols.

A shampoo has, for example, the following composition:
0.1 to 5% wt-% of at least one inventive copolymer
12.0% wt-% of sodium laureth-2-sulfate,
4.0% wt-% of cocamidopropylbetaine,
3.0% wt-% of NaCl and
water to 100 wt-%.

A deodorant has, for example, the following composition:
0.1 to 5% of at least one inventive copolymer
60% by weight of ethanol,
0.3% by weight of perfume oil and
water to 100%.

The new cationic polymers are obtainable by conventional polymerization processes.

The following examples are set forth merely to exemplify the invention and are not intended to limit the metes and bounds of the invention, which is set forth by the claims appended hereto.

Parts and percentages are by weight. The temperatures are stated in degrees Celsius.

Synthesis of the Liquid Dispersion Copolymer

These examples illustrate the preparation of a suitable cationic liquid dispersion copolymer.

EXAMPLE A

An 'aqueous phase' of water soluble components is prepared by admixing together the following components:
0.29 parts of citric acid-1-hydrate,
0.18 parts of a 40% solution of penta sodium diethylene triamine penta acetic
40.77 parts of water
0.01 parts of methylene-bis-acrylamide
11.75 parts of N,N-dimethyl acrylamide (99%)
47.0 parts of methyl chloride quaternised dimethylaminoethylmethacrylate.

An 'oil phase' is prepared by admixing together the following components:
1.7 parts of sorbitan tri-oleate
3.25 parts of a polymeric stabilizer
63.25 parts of a medicinal grade mineral oil
24.7 parts of Isopar® G (dearomatised hydrocarbon solvent; Isopar is a trademark of the Exxon Mobil Corporation)

The two phases are mixed together in a ratio of 1 part oil phase to 1.25 parts aqueous phase under high shear to form a water-in-oil emulsion.

The resulting water-in-oil emulsion is transferred to a reactor equipped with nitrogen sparge tube, stirrer and thermometer. The emulsion is purged with nitrogen to remove oxygen.

Polymerization is effected by addition of a redox couple of sodium metabisulphite and tertiary butyl hydroperoxide.

After the isotherm is completed addition is made of a free radical initiator (Vazo® 67, trademark of DuPont de Nemours and Company)) and the emulsion held at 85° C. for 75 minutes.

Vacuum distillation is carried out to remove water and volatile solvent to give a final product of 50% polymer solids.

To this product addition is made of 8 parts (by weight of final product) of a fatty alcohol alkoxylate (PPG1-trideceth 6).

EXAMPLE B

An 'aqueous phase' of water soluble components is prepared by admixing together the following components:
46.56 parts of dimethylaminomethylmethacrylate (MeCl quaternised) (100%)
11.76 parts of a 99% solution of N,N-dimethylacrylamide
0.29 parts of citric acid
36.84 parts of water
4.37 parts of methylene-bis-acrylamide (1% in water)
0.18 parts of a 40% solution of pentasodiumdiethylenetriaminepenta acetic acid An 'oil phase' is prepared by admixing together the following components:
3.02 parts of sorbitan tri-oleate
3.27 parts of polymeric stabiliser (100%)
50.48 parts of medicinal grade white oil
43.23 parts of high purity dearomatised hydrocarbon solvent The two phases are mixed together in a ratio of 0.80 parts oil phase to 1.0 parts aqueous phase under high shear to form a water-in-oil emulsion.

The resulting water-in-oil emulsion is transferred to a reactor equipped with nitrogen sparge tube, stirrer and thermometer. The emulsion is purged with nitrogen to remove oxygen.

Polymerisation is effected by addition of a redox couple of sodium metabisulphite and tertiary butyl hydroperoxide. After exotherm is complete, free monomer is reduced using the same type of redox initiators.

Vacuum distillation is carried out to remove water and volatile solvent to give a concentrated polymer dispersion.

To this, addition is made of 00.08 parts of a fatty alcohol ethoxylate surfactant.

FORMULATION EXAMPLES

Example 1

Facial Moisturizer

| Ingredient | Amount (wt-%) |
|---|---|
| Aqua | To 100 |
| Copolymer of the Present Invention (synthesis example A) | 2.00 |
| Coco-caprylate/Caprate | 2.50 |
| Squalane | 2.00 |
| Hexyl Laurate | 2.00 |
| Ethylhexyl Palmitate | 2.00 |
| Dimethicone | 2.50 |

Example 2

Body Moisturizer

| Ingredient | Amount (wt-%) |
|---|---|
| Aqua | To 100 |
| Copolymer of the Present Invention (synthesis example A) | 1.00 |
| Stearyl Alcohol | 5.00 |
| Cetyl Alcohol | 5.00 |
| Dimethicone | 5.00 |
| Cetearyl Stearate | 2.00 |
| Glycerin | 2.00 |
| Propylene Glycol | 2.00 |
| Parfum | 0.20 |
| Preservative | 0.20 |

-continued

| Ingredient | Amount (wt-%) |
|---|---|
| Ethylhexyl Methoxycinnamate | 5.00 |
| Parfum | 0.20 |
| Preservative | 0.20 |

Example 3

Spray Moisturizer

| Ingredient | Amount (wt-%) |
|---|---|
| Auqa | To 100 |
| Copolymer of the Present Invention (synthesis example A) | 1.50 |
| Cyclomethicone | 3.00 |
| Hydrogenated Polydecene | 5.00 |
| Isostearyl Lactate | 1.50 |
| Sodium Hyaluronate | 1.00 |
| Glyceryl Myristate | 1.00 |
| Parfum | 0.20 |
| Preservative | 0.20 |

Example 4

Leave-On Conditioner

| Ingredient | Amount (wt-%) |
|---|---|
| Aqua | To 100 |
| Copolymer of the Present Invention (synthesis example A) | 1.50 |
| Propylene Glycol | 2.00 |
| Glycerin | 2.00 |
| Dimethicone Copolyol | 2.00 |
| Preservative | 0.25 |
| Parfum | 0.30 |
| Ethylhexyl Methoxycinnamate | 2.00 |

Example 5

Silicone Conditioner

| Ingredient | Amount (wt-%) |
|---|---|
| Aqua | To 100 |
| Copolymer of the Present Invention (synthesis example A) | 2.00 |
| Cyclopentasiloxane (and) Dimethiconol | 2.00 |
| Cyclomethicone | 2.00 |
| Ceteareth-5 | 0.75 |
| Preservative | 0.20 |
| Dimethicone PEG-8 Meadowfoamate | 0.50 |
| Parfum | 0.20 |

Example 6

Rinse-Off Conditioner

| Ingredient | Amount (wt-%) |
|---|---|
| Aqua | To 100 |
| Copolymer of the Present Invention (synthesis example A) | 2.00 |
| Decyl Oleate | 2.00 |
| Helianthus Annuus | 2.50 |
| Dimethicone (and) Dimethiconol | 2.50 |
| Preservative | 0.20 |
| Parfum | 0.30 |
| CI 18965 | 0.02 |
| Sodium Benzotriazolyl Butylphenol Sulfonate (and) Buteth-3 (and) Tributyl Citrate | 0.20 |

Example 7

Sunless Tanning Cream with Sunscreen

| Ingredient | Amount (wt-%) |
|---|---|
| Aqua | To 100 |
| Copolymer of the Present Invention (synthesis example A) | 2.00 |
| Ethylhexyl Methoxycinnamate | 5.00 |
| Dihydroxyacetone | 3.00 |
| Methylene bis-Benzotriazolyl Tetramethyl Butylphenol | 3.00 |
| Paraffinum Liquidum | 7.50 |
| Preservative | 0.50 |
| Glycerin | 2.00 |
| Parfum | 0.50 |

Example 8

Moisturizing Lipstick

| Ingredient | Amount (wt-%) |
| --- | --- |
| Ricinus Communis | 25.00 |
| Euphorbia Cerifera | 5.40 |
| Copernicia Cerifera | 4.00 |
| Ozokerite | 5.00 |
| Hydrogenated Lanolin | 11.10 |
| Microcrystalline Wax | 4.50 |
| Copolymer of the Present Invention (synthesis example A) | 2.25 |
| Octyldodecanol | 6.60 |
| Isocetyl Palmitate | 5.00 |
| Beeswax | 2.00 |
| Cetearyl Alcohol | 20.00 |
| Preservative | 0.10 |
| Tetradibutyl Pentaerythrityl Hydroxyhydrocinnamate | 0.05 |
| Pigment | 9.00 |

Example 9

Moisturizing Soap Base

| Ingredient | Amount (wt-%) |
| --- | --- |
| Copolymer of the Present Invention (synthesis example A) | 1.00 |
| Sodium Tallowate (and) Sodium Cocoate | 98.10 |
| Tetrasodium EDTA | 0.10 |
| Titanium Dioxide | 0.10 |
| Tetradibutyl Pentaerythrityl Hydroxyhydrocinnamate | 0.05 |
| Parfum | 0.50 |

Example 10

Anti-Acne Skin Cream

| Ingredient | Amount (wt-%) |
| --- | --- |
| Aqua | To 100 |
| Copolymer of the Present Invention (synthesis example A) | 4.00 |
| Alcohol | 5.00 |
| Isocetyl Palmitate | 2.00 |
| Salicylic Acid | 2.00 |
| Paraffinum Liquidum | 1.00 |
| Preservative | 0.50 |
| Glycerin | 2.00 |
| Parfum | 0.50 |

Example 11

Conditioner

| Ingredient | Amount (wt-%) |
| --- | --- |
| Aqua | To 100 |
| Glycerin | 5.00 |
| DMDM Hydantoin | 0.50 |
| Methylparaben | 0.20 |
| Polysorbate 80 | 1.00 |
| Parfum | 0.20 |
| Phenoxyethanol | 0.50 |
| Polyquaternium - 6 | 2.00 |
| Copolymer of the Present Invention (synthesis example A) | 5.60 |

All Formulation Examples 1-11 are also prepared with the copolymer of Example B, whereby the concentrations of each Example are the same.

The invention claimed is:

1. A process of thickening a water- and/or oil based hair conditioner composition by adding a copolymer consisting of the components
   (a) 40-90 wt-% of a cationic monomer of formula (I), $$R_1-CH=C(R_2)-C(=O)-O-(CH_2)_n-N^+(R_3)(R_4)(R_5) \quad Y \quad (I)$$

wherein
$R_1$ and $R_2$ are hydrogen,
$R_3$, $R_4$ and $R_5$ are methyl,
n is 1, 2 or 3, and
Y is a counterion,
and
(b) 10-40 wt-% of a monomer of formula (II)

$$R_6-CH=C(R_7)-C(=O)-N(R_8)(R_9) \quad (II)$$

wherein
$R_6$ signifies hydrogen,
$R_7$ signifies hydrogen, and
$R_8$ and $R_9$ are methyl,
and
   (c) at least one cross-linking agent, which contains at least two ethylenically unsaturated moieties to the hair conditioner composition.

2. The process according to claim 1, wherein the amount of c) is 50-500 ppm, based on the total amount of the copolymer.

3. The process according to claim 1 characterized in that Y is Cl; Br; I; hydrogensulfate or methosulfate.

4. The process according to claim 1, characterized in that (c) is at least one cross-linking agent selected from the group consisting of tetra allyl ammonium chloride;

allyl-acrylamides and allyl-methacrylamides; bisacrylamidoacetic acid and N,N'-methylene-bisacrylamide.

5. The process according to claim 4, wherein the amount of c) is 50-500 ppm, based on the total amount of the copolymer.

6. The process according to claim 1, characterized in that c) is present in an amount of 100-300 ppm, based on the total amount of the copolymer and is selected from tetra allyl ammonium chloride and/or N,N'-methylene-bisacrylamide.

7. The process according to claim 1 which composition comprises:
0.5-10 wt-% of the copolymer,
2-25 wt-% of at least one oil-component,
0-25 wt-% of at least one adjuvant and/or additive, and
water up to 100 wt-%.

8. The process according to claim 1, which composition comprises
0.5-10 wt-% of the copolymer,
50-99 wt-% of at least one oil-component, and
0-25 wt-% of at least one adjuvant and/or additive.

* * * * *